United States Patent [19]

Issler et al.

[11] Patent Number: 4,479,021
[45] Date of Patent: Oct. 23, 1984

[54] CONTINUOUS PROCESS FOR PRODUCING 1,2-ALKANEDIOLS

[75] Inventors: Heinz Issler, Bensheim; Rudolf Maul, Lorsch, both of Fed. Rep. of Germany

[73] Assignee: Ciba-Geigy Corporation, Ardsley, N.Y.

[21] Appl. No.: 527,923

[22] Filed: Aug. 30, 1983

[51] Int. Cl.³ .................. C07C 31/20; C07C 27/02; C07C 29/86
[52] U.S. Cl. .................. 568/868; 568/858
[58] Field of Search .................. 568/858, 860, 868

[56] References Cited

U.S. PATENT DOCUMENTS

| | | | |
|---|---|---|---|
| 2,138,917 | 12/1938 | Grun | 568/868 |
| 2,492,201 | 12/1949 | Swern et al. | 568/860 |
| 2,739,173 | 3/1956 | Corey et al. | 568/858 |
| 2,808,429 | 10/1957 | Cosby et al. | 568/858 |
| 4,404,410 | 9/1983 | Cornils et al. | 568/858 |

FOREIGN PATENT DOCUMENTS

| | | | |
|---|---|---|---|
| 0025940 | 4/1981 | European Pat. Off. | 568/858 |
| 22305 | 2/1979 | Japan | 568/868 |
| 331055 | 4/1972 | U.S.S.R. | 568/868 |

Primary Examiner—J. E. Evans
Attorney, Agent, or Firm—Karl F. Jorda

[57] ABSTRACT

There is described a continuous process for producing 1,2-alkanediols of the formula

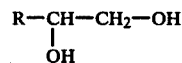

in which R is an alkyl group having 3–6 carbon atoms, by reaction of a 1-alkene of the formula

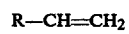

in which R is as defined above, with formic acid and hydrogen peroxide, and subsequent saponification of the formed alkanediol monoformate, which process is performed in several consecutive reaction stages.

The 1,2-alkanediols of the above formula obtainable by the process are intermediates for the production of pesticides.

17 Claims, No Drawings

CONTINUOUS PROCESS FOR PRODUCING 1,2-ALKANEDIOLS

The present invention relates to a continuous process for producing 1,2-alkanediols of the formula I $$R-\underset{\underset{OH}{|}}{CH}-CH_2-OH \quad (I)$$

in which R is an alkyl group having 3-6 carbon atoms.

The 1,2-alkanediols of the formula I are valuable intermediates for producing 1-($\beta$-arylethyl)-1H-1,2,4-triazole ketals having an antimicrobic action and an action regulating plant growth. Such 1-($\beta$-arylethyl)-1H-1,2,4-triazole ketals, the production thereof and their use are described for example in the U.S. Pat. No. 4,079,062. An important representative of this class of substances to be mentioned is the 1-[2-(2,4-dichlorophenyl)-4-n-propyldioxalan-2-ylmethyl]-1H-1,2,4-triazole, which is known under the name of Propiconazol. It can be produced by reaction of ω-bromo-2,4-dichloroacetophenone with 1,2-pentanediol to give 2-bromomethyl-2-(2,4-dichlorophenyl)-4n-propyldioxolane, and the further reaction thereof with 1H-1,2,4-triazole.

It is known that 1-alkenes, such as 1-octene, 1-decene, 1-dodecene, 1-tetradecene, 1-hexadecene and 1-octadecene, can be converted, by reaction with peroxyformic acid in formic acid as solvent, and subsequent alkaline saponification of the firstly formed 1,2-alkanediol monoformates, into the corresponding 1,2-alkanediols. The required peroxyformic acid in this case is not produced separately but is produced directly in the reaction mixture. The procedure is such that there is introduced at about 40° C. into a mixture consisting of the 1-alkene and formic acid, with stirring, the necessary amount of hydrogen peroxide, the formic acid being used in an amount of 10-30 mols per mol of 1-alkene, and aqueous hydrogen peroxide at a concentration of about 25% by weight. The reaction time under these conditions is 8-24 hours (cp. J. Amer. Chem. Soc. 68 (1946), 1504-1507). According to European patent application No. 25.940, this process is improved by using 2-6 mols of formic acid per mol of 1-alkene, and hydrogen peroxide at a concentration of 35-98% by weight, and performing the reaction at a temperature of 40°-80° C.

Finally, there is described in the German patent application No. 2,937,840 a process in which less than 2 mols of formic acid per mol of alkene and less than 2 mols of hydrogen peroxide are used, the concentration of formic acid that can be used being 20-100% by weight, and the concentration of the employed hydrogen peroxide being below 50% by weight.

The aforementioned processes are all performed by taking a mixture of 1-alkene and formic acid, and, with vigorous stirring, introducing the necessary amount of hydrogen peroxide. This procedure is disadvantageous for carrying out the process on a large scale in that the starting mixture at the commencement of the reaction is in 2 phases on account of the low solubility of the 1-alkenes used as starting materials in formic acid. The complete intermixing of such mixtures, which is essential for a smooth course of reaction, is very difficult when the process is performed on a commercial scale, and is possible only with a high expenditure. Furthermore, the known procedure for the reaction of lower 1-alkene is disadvantageous also in that it is necessary, on account of the low boiling point of these compounds, to carry out the reaction either at very low temperatures or under pressure. It is therefore not possible with the prior known processes to produce the 1,2-alkanediols of the formula I on a commercial scale in a simple and economic manner.

It was the object of the present invention to provide a process for producing 1,2-alkanediols of the formula I which would avoid the disadvantages of the known processes and which would render possible the production of the 1,2-alkanediols of the formula I in a simple and economic manner on a commercial scale.

There is suggested according to the present invention a continuous process for producing 1,2-alkanediols of the formula I by reaction of a 1-alkene of the formula II $$R-CH=CH_2 \quad (II),$$

in which R is as defined under the formula I, with formic acid and hydrogen peroxide, and subsequent saponification of the formed alkanediol monoformate, which process is performed in several consecutive reaction stages, the procedure being such that the amount of reactants and/or reaction mixture being fed into a reaction stage always corresponds to the amount of reaction mixture being removed; and that the 1-alkene of the formula II, formic acid and hydrogen peroxide are introduced in controlled amounts in the molar ratio of 1.0:0.8-2.0:1.0-1.5, at a temperature of 0°-60° C., into the first stage; that the reaction mixture leaving the first reaction stage is held at 30°-60° C. in a second reaction stage; and that the reaction mixture emerging from the second reaction stage is transferred to a third reaction stage in which a temperature of 60°-80° C. and, by the addition of concentrated aqueous alkali, a pH value of 10-11 are maintained; and that from the reaction mixture leaving the third reaction stage the formed 1,2-alkanediol of the formula I is separated by extraction with an organic solvent and obtained from the extract by removal of the solvent by distillation.

The 1-alkenes of the formula II are obtainable commercially in a degree of purity of above 90%, and they can be used directly in this form. Suitable 1-alkenes of the formula II are for example: 1-pentene, 1-hexene, 1-heptene, 1-octene, 3-methyl-1-pentene, 4-methyl-1-pentene, 3-methyl-1-hexene, 2,4-dimethyl-1-pentene and 2,5-dimethyl-1-hexene. A preferred 1-alkene of the formula II is 1-pentene.

The formic acid can be used in an anhydrous or aqueous form. Formic acid at a concentration of 70-100% is used as a rule, and within this concentration range preferably a formic acid at a concentration of 80-96%.

In carrying out the process according to the invention, it has proved advantageous to add 0.5-6% by weight of sulfuric acid to the formic acid. The sulfuric acid can be added in the concentrated form or in a moderately diluted form. A sulfuric acid diluted to the extent of approximately 50% is advantageously added. The sulfuric acid can either be added to the formic acid before introduction into the reaction vessel, or be fed in a corresponding amount into the reaction vessel simultaneously with the formic acid.

The hydrogen peroxide can be used in the pure form or as a moderately diluted aqueous solution. Hydrogen peroxide at a concentration of 50-100% can as a rule be used, but preferably hydrogen peroxide at a concentration of 70–75% is used.

Within the already stated range for the molar ratio of 1-alkene of the formula II to formic acid and hydrogen peroxide of 1.0:0.8–2.0:1.0–1.5, preferred molar ratios of 1-alkene of the formula II to formic acid and hydrogen peroxide are 1.0:1.2–1.5:1.2–1.5.

Within the given ranges for the reaction temperature in the individual stages, there is preferred in the first stage a reaction temperature of 30°–60° C., in the second stage a temperature of 45°–60° C. and in the third stage a temperature of 65°–75° C.

The multistage reactor in which the process according to the invention is performed consists as a rule of several consecutive individual reactors which are advantageously arranged as an agitator vessel cascade. The process according to the invention comprises essentially 3 stages, namely a first stage in which the introduction of the reactants in controlled amounts to form the reaction mixture is carried out, a second stage in which the reaction mixture obtained after the introduction of the reactants is maintained under defined reaction conditions until the course of the reaction is completed, and a third stage in which the alkanediol monoformate firstly formed is hydrolytically cleaved to give the 1,2-alkanediol of the formula I, after which the reaction mixture is further processed by extraction and subsequent distillation of the extract. A process stage can consist of one agitator vessel or can be spread over several agitator vessels. The number of agitator vessels used is determined essentially by the throughput and the required holding time. The size of the individual agitator vessels is as a rule such that by a calculation based on the throughput and the volume of the individual vessel there results a holding time of 4–8 hours. The individual units are usually of equal size. Units differing in size can however also be used.

The introduction in controlled amounts of all the reactants can in the simplest case be effected in the first vessel. It is however also possible, and in many cases advantageous, to spread the introduction of the reactants over two or more vessels. In this case the procedure advantageously is to feed the entire amount of formic acid and optionally sulfuric acid into the first vessel, but to introduce the alkene of the formula II and the hydrogen peroxide into two or more vessels. The total amount of 1-alkene of the formula II and hydrogen peroxide to be added is then as a rule evenly divided according to the number of vessels in which the introduction of these components is to be carried out.

The second stage in which the reaction mixture, after completion of the addition of all the components, is allowed to fully react can likewise consist of one or more agitator vessels. The reaction temperature used in the second stage is generally higher than that in the first stage. It is advantageous when the reaction temperature in the second stage is such that unreacted 1-alkene of the formula II can be distilled off from the reaction mixture and fed back into the first stage.

In the third stage, which can likewise consist of one or more agitator vessels, there is added to the fully reacted reaction mixture, which has been freed from unreacted 1-alkene of the formula II, aqueous alkali in such an amount that a pH-value of 10–11 results. The aqueous alkali used is a concentrated solution of an alkali metal hydroxide, for example sodium hydroxide or potassium hydroxide, or of an alkali carbonate or alkali hydrogen carbonate, for example sodium carbonate, potassium carbonate, sodium hydrogen carbonate and potassium hydrogen carbonate.

From the reaction mixture emerging from the last vessel of the agitator vessel cascade, the formed 1,2-alkanediol of the formula I is separated by extraction with a suitable solvent. Suitable solvents are aliphatic and aromatic hydrocarbons and halogenated hydrocarbons, esters and ketones. Solvents which are suitable are for example: methylene chloride, chloroform, carbon tetrachloride, 1,2-dichloroethane, toluene, chlorobenzene, ethyl acetate, butyl acetate, methyl ethyl ketone, methyl isobutyl ketone and methyl-tert-butyl ketone. Particularly suitable solvents are: methylene chloride, chloroform, ethyl acetate, methyl-isobutyl ketone and methyl-tert-butyl ketone. Especially preferred solvents are methyl-isobutyl ketone and methyl-tert-butyl ketone.

The extraction is advantageously performed continuously in an extraction column, in which the reaction mixture and the solvent are brought together by the countercurrent principle. The 1,2-alkanediol of the formula I is obtained from the extract by distilling off the solvent. This distillation can be performed in a customary distillation column, for example in a packed column, bell column or sieve plate column. The solvent is advantageously removed in a thin-layer evaporator. The crude product resulting after removal of the solvent can be purified by distillation.

In putting the agitator vessel cascade into operation, it is advantageous to feed into the first vessel formic acid to which optionally an appropriate amount of sulfuric acid has been added, and to simultaneously introduce in controlled amounts the alkene and the hydrogen peroxide under the given conditions. When the alkene and hydrogen peroxide have been introduced in an amount corresponding to the molar ratio at which the reaction is to be performed in the vessel concerned, there is commenced the further feeding in of formic acid and optionally sulfuric acid with the simultaneous transfer to the next vessel of an amount of reaction mixture corresponding to the amount of reactants fed into the first vessel, it being then possible at the same time to add fresh alkene and hydrogen peroxide to the reaction mixture.

The reactants can be fed in controlled amounts into the reactor either individually or as a premix. When feeding in the reactants as a premix, they are mixed together with a high turbulence in a mixing chamber located in front of the reactor, and are fed from the mixing chamber directly into the reactor. In the case where there is used a reactor in front of which is provided a mixing chamber for the reactants, a stirring device in the reactor itself can be dispensed with. It is possible therefore in this case to use, besides agitator vessels, other reactors, for example a tube reactor. It is then of course advantageous to use for each of the process stages at least one reactor unit, and to pass the reaction mixture, when it is being transferred from one unit to the other, in each case through a mixing chamber, into which at the same time further starting material can be fed.

It is possible with the process according to the invention to produce 1,2-alkanediols of the formula I in a simple and economical manner and in excellent yield and degree of purity. A particular advantage of the process according to the invention is that the reaction mixture remains as a single phase. This is largely also the case when disturbances occur on account of possible overfeeding or underfeeding, since such disturbances are buffered by virtue of the multistage procedure according to the invention. The whole system when carried out according to the invention in a multistage reactor is hence considerably less affected by irregularities in operation than it would be in a single-stage reactor.

A further important advantage of the process according to the invention is that also lower alkenes of the formula II, such as 1-pentene or 1-hexene, can be reacted without the application of excess pressure at temperatures which are clearly above the boiling point of these substances. 1-Pentene for example can be easily reacted under normal pressure at temperatures of up to 60° C. without the substance volatilising out of the reaction mixture. The process of the invention is thus suitable in particular for the reaction of lower alkenes of the formula II. An additional advantage of the process according to the invention results finally from the use of hydrolysis of the firstly formed alkanediol monoformates, since with this procedure both the separation of the formic acid by distillation and the decomposition of excess hydrogen peroxide can be dispensed with.

The process according to the invention is further illustrated by the following Example.

EXAMPLE

Production of 1,2-pentanediol

The employed reactor is an agitator vessel cascade consisting of 4 agitator vessels. The individual vessels R1, R2, R3 and R4 are provided with a stirrer, a heating or cooling jacket, dosing devices for the reactants or the reaction mixture from the preceding vessel and a bottom outlet. R1 and R2 are also fitted with a reflux condenser, and R3 with a distillation head for distilling off the unreacted 1-pentene. R1 and R2 each have a volume of 2 liters, R3 a volume of 0.5 liter and R4 a volume of 1 liter.

The starting materials formic acid and sulfuric acid are fed completely into R1, whilst the addition of 1-pentene and hydrogen peroxide is divided between R1 and R2. During the operation, there is maintained in R1 and R2 a temperature of 40°–50° C., in R3 (subsequent reactor) a temperature of 50°–55° C., and in R4 (saponification reactor) a temperature of 70° C. The 1-pentene distilled off from R3 is recycled into R1 and R2, and the reaction mixture emerging from R4 is passed in countercurrent to ethyl acetate through an extraction column, and the extract is freed in a distillation column from the solvent and fractionated.

| Flow of substances in R1 | | |
|---|---|---|
| 1-pentene (95%) | 47.0 g/h | 0.64 mol/h |
| formic acid (85%) | 99.0 g/h | 1.83 mol/h |
| hydrogen peroxide (70%) | 44.0 g/h | 0.91 mol/h |
| sulfuric acid (50%) | 3.0 g/h | 0.02 mol/h |
| Flow of substances in R2 | | |
| reaction mixture from R1 | | |
| 1-pentene (95%) | 47.0 g/h | 0.64 mol/h |
| hydrogen peroxide (70%) | 44.0 g/h | 0.91 mol/h |
| Flow of substance in R3 | | |
| reaction mixture from R2 | | |
| Flow of substances in R4 | | |
| reaction mixture from R3 | | |
| sodium hydroxide (50%) | ~154 g/h | ~1.93 mol/h |
| Flow of substances in extraction | | |
| reaction mixture from R4 | | |
| ethyl acetate | ~650 g/h | |
| Flow of substance in distillation | | |
| extract | ~750 g/h | |
| 1,2-Pentanediol | 93.0 g/h | 0.89 mol/h | yield: 70% of theory, relative to 1-pentene.

What is claimed is:

1. A continuous process for producing a 1,2-alkanediol of the formula I

in which R is an alkyl group having 3–6 carbon atoms, by reaction of a 1-alkene of the formula II

in which R is as defined under the formula I, with formic acid and hydrogen peroxide, and subsequent saponification of the formed alkanediol monoformate, which process is performed in several consecutive reaction stages, the procedure being such that the amount of reactants and/or reaction mixture being fed into a reaction stage always corresponds to the amount of reaction mixture being removed; and that the 1-alkene of the formula II, formic acid and hydrogen peroxide are introduced in controlled amounts in the molar ratio of 1.0:0.8–2.0:1.0–1.5, at a temperature of 0°–60° C., into the first stage; that the reaction mixture leaving the first reaction stage is held at 30°–60° C. in a second reaction stage; and that the reaction mixture emerging from the second reaction stage is transferred to a third reaction stage in which a temperature of 60°–80° C. and, by the addition of concentrated aqueous alkali, a pH value of 10–11 are maintained; and that from the reaction mixture leaving the third reaction stage the formed 1,2-alkanediol of the formula I is separated by extraction with an organic solvent and obtained from the extract by removal of the solvent by distillation.

2. A process according to claim 1, wherein 70–100% formic acid is used.

3. A process according to claim 1, wherein 80–96% formic acid is used.

4. A process according to claim 1, wherein 0.5–6% by weight of sulfuric acid is added to the formic acid used.

5. A process according to claim 1, wherein hydrogen peroxide at a concentration of 50–100% is used.

6. A process according to claim 1, wherein 70–75% hydrogen peroxide is used.

7. A process according to claim 1, wherein the 1-alkene of the formula II, formic acid and hydrogen peroxide are used in a molar ratio of 1.0:1.2–1.5:1.2–1.5.

8. A process according to claim 1, wherein there is used in the first stage a reaction temperature of 30°–60° C., in the second stage a temperature of 45°–60° C. and in the third stage a temperature of 65°–75° C.

9. A process according to claim 1, wherein the pH value of the reaction mixture is adjusted to 10–11 by the addition of a concentrated aqueous solution of an alkali metal hydroxide, alkali metal carbonate or alkali metal hydrogen carbonate.

10. A process according to claim 1, wherein the pH value of the reaction mixture is adjusted to 10–11 by the addition of a concentrated aqueous solution of an alkali metal hydroxide, particularly by the addition of 50% sodium hydroxide solution.

11. A process according to claim 1, wherein the formed 1,2-alkanediol of the formula I is separated from the reaction mixture by extraction with a solvent selected from the group comprising aliphatic and aromatic hydrocarbons and halogenated hydrocarbons, esters and ketones.

12. A process according to claim 1, wherein the formed 1,2-alkanediol of the formula I is separated from the reaction mixture by extraction with methylene chloride, chloroform, carbon tetrachloride, 1,2-dichloroethane, toluene, chlorobenzene, ethyl acetate, butyl acetate, methyl ethyl ketone, methyl isobutyl ketone or methyl-tert-butyl ketone.

13. A process according to claim 1, wherein the formed 1,2-alkanediol of the formula I is separated from the reaction mixture by extraction with methylene chloride, chloroform, ethyl acetate, methyl isobutyl ketone or methyl tert-butyl ketone.

14. A process according to claim 1, wherein the formed 1,2-alkanediol of the formula I is separated from the reaction mixture by extraction with methyl isobutyl ketone or methyl tert-butyl ketone.

15. A process according to claim 1, wherein 1-pentene is used as 1-alkene of the formula II.

16. A process according to claim 1, wherein the reactor used is an agitator vessel cascade.

17. A process according to claim 1, wherein the entire amount of formic acid and optionally sulfuric acid is fed into the first vessel and the alkene of the formula II and the hydrogen peroxide is introduced into two or more vessels.

* * * * *